US006177135B1

(12) United States Patent
Hintermaier et al.

(10) Patent No.: US 6,177,135 B1
(45) Date of Patent: *Jan. 23, 2001

(54) LOW TEMPERATURE CVD PROCESSES FOR PREPARING FERROELECTRIC FILMS USING BI AMIDES

(75) Inventors: Frank S. Hintermaier, Munich (DE); Peter C. Van Buskirk, Newtown, CT (US); Jeffrey F. Roeder, Brookfield, CT (US); Bryan C. Hendrix, Danbury, CT (US); Thomas H. Baum, New Fairfield, CT (US); Debra A. Desrochers, Brookfield, CT (US)

(73) Assignee: Advanced Technology Materials, Inc., Danbury, CT (US)

( * ) Notice: Under 35 U.S.C. 154(b), the term of this patent shall be extended for 0 days.

This patent is subject to a terminal disclaimer.

(21) Appl. No.: 09/208,542

(22) Filed: Dec. 9, 1998

Related U.S. Application Data

(63) Continuation-in-part of application No. 08/828,566, filed on Mar. 31, 1997, now Pat. No. 5,902,639
(60) Provisional application No. 60/069,041, filed on Dec. 10, 1997.

(51) Int. Cl.⁷ .................................................. C23C 16/40
(52) U.S. Cl. .................... 427/255.31; 427/314; 427/576; 427/595
(58) Field of Search ............................. 427/255.32, 314, 427/576, 596, 81, 255.31, 595

(56) References Cited

U.S. PATENT DOCUMENTS

| 5,478,610 | 12/1995 | Desu et al. . |
|---|---|---|
| 5,527,567 | 6/1996 | Desu et al. . |
| 5,902,639 | * 5/1999 | Glassman et al. ................ 427/248.1 |

FOREIGN PATENT DOCUMENTS

| 747937 | 11/1996 | (EP) . |
|---|---|---|
| 747938 | 11/1996 | (EP) . |
| 9067197 | 4/1995 | (JP) . |
| 8277197 | 8/1995 | (JP) . |
| 8339716 | 8/1995 | (JP) . |
| 9077592 | 9/1995 | (JP) . |
| WO 95/02897 | 1/1995 | (WO) . |

OTHER PUBLICATIONS

T. Li, et al., "The microstructure and properties for layered oxide thin films fabricated by MOCVD" Mat. Res. Soc. Symp. Proc. vol. 415 [1996], p. 189.

T. Li et al., "Metalorganic chemical vapor deposition of ferroelectric $SrBi_2Ta_2O_9$", Appl. Phys. Lett. 68(5) [1996], p. 616.

T. Ami et al., "Preparation and properties of ferroelectric $Bi_2SrTa_2O$ thin films for FeRAM using flash–MOCVD" Mat. Res. Soc. Symp. Proc. vol. 415, [1995], p. 195.

C. Isobe et al., "Characteristics of ferroelectric $SrBi_2Ta_2O_9$ thin films grown by flash MMOCVD" Integrated Ferroelectrics, vol. 14, pp. 95–103 [1997].

R. Gardiner et al., "Liquid delivery of low vapor pressure MOCVD precursors", Mat. Res. Soc. Symp. Proc. 335, 221, [1994].

Van Buskirk et al., "Plasma–enhanced metalorganic chemical vapor deposition of $BaTiO_3$ films" J. Vac. Sci. Tech. A, 10(4). 1578 [1992].

T. Nakamura et al., "Preparation of $Bi_4Ti_3O_{12}$ Films by MOCVD and their application to memory devices", Integrated Ferroelectrics, vol. 6, pp. 35–46, [1995].

Clegg et al, "X–ray Crystal Structure of $[Bi(NMe_2)_3]$", Inorganic Chemistry, vol. 30 (24), pp. 4680–4682 [1991].

H. Suzuki et al, "Ultrasonic reaction of triarylbismuthines and tri arylstibines with Iodosylbenzene. Mild oxidizing ability of the organobismuth oxide function for organic substrates." Tetrahedron Letters, vol. 35, No. 44 [1994], pp. 8197–8200.

Y. Okuhara et al., "Development of new Ferroelectric Source Materials for MOCVD and MOD" Int Symp. For Int. Ferroelectrics, Mar. 1997, Book of Abstracts, 133i, 9$^{th}$ International Symposium on Integrated Ferroelectrics.

G. Lucovsky et al., "Deposition of silicon dioxide and silicon nitride by remote plasma enhanced chemical vapor deposition", J. Vac. Sci. Tech. A, vol. 4, 681, [1986].

A.P.Pisarevskii, et al, "Bismuth Carboxylates", Russ. Journ. of Inorg. Chem., vol. 35, (6) 1990, pp. 84–85.

K. Yoshimura et al, "Preparation of ferroelectric $Bi_4Ti_3O_{12}$ thin films with c–axis orientation by atmospheric pressure metal organic chemical vapor deposition" Jpn. J. Appl. Phy. vol. 34, [1995], pp. 2425–2429.

Y. Kojima, et al, "Measurements of vapor pressures of MOCVD materials, which are usable for ferroelectric thin films", Integrated Ferroelectrics, 1997, vol. 18, pp. 183–195.

R.G. Goel et al., "Organobismuth compounds The Preparation and structural characteristics of triphenylbismuth(V) compounds containing a Bi–O–Bi Bond.", J. Organomet. Chem. 36, p. 323 (1972).

W.A. Hermann et al, "Volatile Metal Alkoxoides according to the concept of donor functionalization" Angewandte Chemie, vol. 34, 1995, pp. 2187–2206.

* cited by examiner

*Primary Examiner*—Timothy Meeks
*Assistant Examiner*—Bret Chen
(74) *Attorney, Agent, or Firm*—Oliver A.M. Zitzmann; Steven J. Hultquist

(57) ABSTRACT

Chemical vapor deposition is used to form a film of Bi oxide, Sr oxide, and Ta oxide on a heated substrate by decomposing the precursors of these oxides at the surface of the substrate. The precursor of Bi oxide is a Bi complex which includes at least one amide group and is decomposed and deposited at a temperature lower than 450° C. The film of Bi, Sr, and Ta oxides obtained by low-temperature CVD is predominantly non-ferroelectric, but can be converted into a ferroelectric film by a subsequent heating process.

68 Claims, 6 Drawing Sheets

POWDER XRD OF α−Bi$_2$O$_3$ FROM OXIDATION OF Bi(N(SiMe$_2$)$_3$) AFTER HEATING TO 500 °C

EDS OF OXIDATION PRODUCT OF Bi(N(SiMe$_3$)$_2$)$_3$

LOW TEMPERATURE CVD PROCESSES FOR PREPARING FERROELECTRIC FILMS USING BI AMIDES

CROSS REFERENCE TO RELATED APPLICATIONS

This application is a continuation-in-part of U.S. patent application Ser. No. 08/828,566 filed Mar. 31, 1997, entitled "Method of Forming Bismuth-Containing Films by Using Bismuth Amide Compounds," and now issued as U.S. Pat. No. 5,902,639.

This application claims the benefit of U.S. Provisional Application No. 60/069,041, filed Dec. 10, 1997, entitled "A CVD process using Bi amide precursors for the preparation of Bi ceramic thin-films for integration into ferroelectric memory devices."

This application is related to U.S. Ser. No. 08/975,087, filed Nov. 17, 1997, entitled "Low Temperature Chemical Vapor Deposition Process for Forming Bismuth-containing Thin Films Useful in Ferroelectric Memory Devices."

This application is related to co-pending applications U.S. Ser. No. 09/208,541, filed Dec. 9, 1998, entitled "Low-temperature CVD processes for preparing ferroelectric films using Bi alcoxides," U.S. Ser. No. 09/208,544, filed Dec. 9, 1998 entitled "Low-temperature is CVD processes for preparing ferroelectric films using Bi aryls," and U.S. Ser. No. 09/208,543, filed Dec. 9, 1998, entitled "Low-temperature CVD processes for preparing ferroelectric films using Bi carboxylates."

BACKGROUND OF THE INVENTION

This invention relates to chemical vapor deposition methods for providing a Bi oxide-containing film on a surface of a substrate by decomposing a precursor of Bi oxide.

Interest in ferroelectrics has increased in recent years, due to the utility of these materials in applications such as non-volatile memories. Information in these memories is stored by the polarization of a thin ferroelectric film which is placed between the two plates of a capacitor. The capacitor is connected to a transistor to form a storage cell, which controls the access of read-out electronics to the capacitor.

The information stored in the cell can be changed by applying an electric field to the thin ferroelectric film and flipping the polarization. Ferroelectric random access memories (FERAMs), unlike DRAMs (dynamic random access memories), retain the stored information if the power supply is turned off. In addition, they do not require refresh cycles. Desirable electrical properties for ferroelectrics used in memory applications include: (a) a low coercive field, which makes the use of as low a voltage supply as possible; (b) a high remanent polarization, which is needed for high reliability of information storage; (c) minimal fatigue, which is required for a long life-time; and (d) no imprint, as an imprint would alter the stored information.

Strontium bismuth tantalate ($SrBi_2Ta_2O_9$) (SBT) is a ferroelectric material that meets all of these requirements. Significant efforts are therefore being made to integrate this material into memory devices. Capacitors in which SBT is incorporated using a sol-gel method have good electrical properties. The sol-gel method provides only a low integration density of SBT, however. To achieve a higher integration density of SBT, an alternative method, such as chemical vapor deposition (CVD), must be used.

SUMMARY OF THE INVENTION

In one aspect, the invention features a method of forming a Bi-containing metal oxide film on a substrate; the method include decomposing a precursor of Bi oxide and depositing the Bi oxide on the substrate. Bi complexes which include at least one amide group are used as the precursors of Bi oxide.

Embodiments of this aspect of the invention may include one or more of the following features.

The precursor of Bi oxide is dissolved in a solution prior to being decomposed. The deposition temperature is preferably lower than 450° C., and is more preferably lower than 400° C. The Bi oxide-containing film may also be provided by adding the step of decomposing a precursor of Sr oxide and a precursor of Ta oxide to form Sr oxide and Ta oxide, respectively, and depositing the Bi oxide, the Sr oxide and the Ta oxide on the substrate.

The Bi-containing metal oxide film may be deposited as a ferroelectric film or can be converted into a ferroelectric film by an annealing process.

The Bi-containing metal oxide film is formed by placing the substrate in a CVD chamber, heating the substrate to a deposition temperature lower than 450° C., introducing vapors of the precursors of Bi, Sr, and Ta oxides to the CVD chamber, decomposing the precursors of Bi, Sr, and Ta oxides, and depositing the oxides on the substrate. Precursors of Bi, Sr, and Ta oxides may be decomposed in the presence of an oxidizer by oxidative decomposition, where examples of the oxidizers include $O_2$, singlet $O_2$, $O_3$, $H_2O_2$, $N_2O$, $NO_x$ ($1 \leq x \leq 3$), and downstream oxygen plasma, and where the concentration of the oxidizer is between 5% and 95% of the total gas and vapor flow into the CVD chamber. At least one of $O_2$ and $N_2O$ may be used as the oxidizer. The oxidizer may be formed in the CVD chamber by converting an oxidizer molecule into an active oxidizer by applying to the CVD chamber plasma, UV light, heat, a sensitizer, or ion beams.

The precursor of Bi oxide may have the formula $Bi(NR_2)_3$, $Bi(NR_2)_2(L)$, where L is NR", alcoxyamine, alkylene diamine, or β-ketoamidate, or $Bi(NRR')_3$, where each of R, R', and R" is, independently, an alkyl group, an aryl group, or a silyl group. For example, each of R and R' may be, independently, $^t$pentyl, pentyl, $^t$Bu, Bu, $^i$Pr, Pr, Et, Me, Ph, aryl, or SiR'''$_3$, and R''' may be $^t$Bu, Bu, $^i$Pr, Pr, Et, or Me. Examples of precursors of Bi oxide include $Bi(NMe_2)_3$ and $Bi(NEt_2)_3$. The precursor of Bi oxide may also include an alkoxy group, or a donor atom such as N, O, or S; for example, the precursor may include the group —$CH_2CH_2$—$N(CH_3)_2$.

The Bi-containing metal oxide deposited on the substrate may have the formula $(Bi_2O_2)^{2+}(A_{m-1}B_mO_{3m+1})^{2-}$, where A is $Bi^{3+}$, $L^{3+}$, $L^{2+}$, $Ca^{2+}$, $Sr^{2+}$, $Ba^{2+}$, $Pb^{2+}$, or $Na^+$, B is $Fe^{3+}$, $Al^{3+}$, $Sc^{3+}$, $Y^{3+}$, $L^{3+}$, $L^{4+}$, $Ti^{4+}$, $Nb^{5+}$, $Ta^{5+}$, $W^{6+}$, or $Mo^{6+}$, and L is $Ce^{4+}$, $La^{3+}$, $Pr^{3+}$, $Ho^{3+}$, $Eu^{2+}$, or $Yb^{2+}$, and where $1 \leq m \leq 5$. The Bi-containing metal oxide may also have the formula $Bi_2WO_6$; $BiMO_3$, where M is Fe or Mn; $Ba_2BiMO_6$, where M is V, Nb or Ta; $Pb_2BiMO_6$, where M is V, Nb or Ta; $Ba_3Bi_2MO_9$, where M is Mo or W; $Pb_3Bi_2MO_9$, where M is Mo or W; $Ba_6BiMO_{18}$, where M is Mo or W; $Pb_6BiMO_{18}$, where M is Mo or W; $KBiTi_2O_6$; or $K_2BiNb_5O_{15}$. These metal oxides can be obtained by decomposing precursors which contain the above-described metals.

The Bi-containing metal oxide film can also be a SBT derivative. Examples of such derivatives include $SrBi_2Ta_2O_9$; $SrBi_2Ta_{2-x}Nb_xO_9$, where $0 \leq x \leq 2$; $SrBi_2Nb_2O_9$; $Sr_{1-x}Ba_xBi_2Ta_{2-y}Nb_yO_9$, where $0 \leq x \leq 1$ and $0 \leq y \leq 2$; $Sr_{1-x}Ca_xBi_2Ta_{2-y}Nb_yO_9$ where $0 \leq x \leq 1$ and $0 \leq y \leq 2$; $Sr_{1-x}Pb_xBi_2Ta_{2-y}Nb_yO_9$, where $0 \leq x \leq 1$ and $0 \leq y \leq 2$; or $Sr_{1-x-y-z}Ba_xCa_yPb_zBi_2Ta_{2-p}Nb_pO_9$, where $0 \leq x \leq 1$, $0 \leq y \leq 1$, $0 \leq z \leq 1$, and $0 \leq p \leq 2$. An element of the metal oxide may be substituted by a metal such as Ce, La, Pr, Ho, Eu, and Yb.

The precursor of Sr oxide generally has the formula $Sr(thd)_2$ or $Sr(thd)_2$ adduct, and may include a polyether or a polyamine. The polyether has the formula R—O—$(CH_2CH_2O)_n$—R', where $2 \leq n \leq 6$, and where each of R and R' may be, independently, an alkyl group, an aryl group, or hydrogen. The polyamine has the formula R—NR"—$(CH_2CH_2NR")_n$—R', where $2 \leq n \leq 6$, where each of R and R' may be, independently, an alkyl group, an aryl group, or hydrogen, and where R" is H, Me, Et, or Pr. The precursor of Sr oxide may also include tetraglyme, triglyme, N,N,N', N",N"-pentamethyl-diethylene-triamine, or N,N,N',N",N"', N"'-hexamethyl-triethylene-tetramine.

The precursor of Ta oxide generally has the formula $Ta(OR)_{5-n}(X)_n$, where R is Me, Et, Pr, $^i$Pr, Bu, $^i$Bu, $^t$Bu, pentyl, or $^i$pentyl, where X is β-diketonate, and where $1 \leq n \leq 5$. For example, the precursor may be $Ta(O^iPr)_4(thd)$.

The precursors of the Bi, Sr, and Ta oxides are dissolved in a solution of an aliphatic, a cycloaliphatic, or an aromatic solvent that may include a functional group such as an alcohol, ether, ester, amine, ketone, or aldehyde group. For example, the precursors of Bi, Sr, and Ta oxides may be dissolved in a solvent such as octane. Alternatively, the precursors may be dissolved in a mixture of THF, $^i$PrOH, and tetraglyme in a ratio of about 8:2:1, respectively, or a mixture of octane, decane, and pentamethyl-diethylene-triamine in a ratio of about 5:4:1. Butyl acetate may be used as the solvent for the precursors of Sr and Ta oxides, and octane for the precursor of Bi oxide.

The solutions containing the precursors are evaporated by vaporizers. For example, the solution containing the precursor of Bi oxide is evaporated at a temperature from 130° C. to 300° C., and the solution for the precursors of Sr and Ta oxides is evaporated at a temperature from 170° C. to 240° C. An inert gas such as Ar, He, or $N_2$ is added to the vapors of the solution, and a mixture of the inert gas and vapors is delivered to the CVD chamber. For example, the mixture includes vapors of the precursors of Bi oxide, Sr oxide, and Ta oxide in a ratio of about 2:1:2. It is appreciated that the concentrations of the precursors in the vapor mixture depend on several factors including vaporization temperature, pressure in the vaporizer, gas and vapor flow rate, desired film stoichiometry, and geometry of the CVD chamber.

In the CVD chamber, the substrate is heated to the deposition temperature of 300° C. to 450° C. The pressure in the CVD chamber is maintained between 0.001 torr and 760 torr, for example, between 0.1 torr and 10 torr. An additional inert gas is added to the CVD chamber, where the concentration of the inert gas may vary from 10% to 90% of the total gas and vapor flow into the CVD chamber, for example, 30% to 50%. Preferably, the vapors of the precursors, the oxidizers, and an inert gas are introduced to the CVD chamber at a total flow rate of 1 ml/min to 15,000 ml/min, measured at the standard condition. The desirable flow rate may also depend on the temperature and pressure of the gas and vapor mixture, desired film stoichiometry, and geometry of the CVD chamber. The oxides are deposited onto the substrate over a time period between 2 minutes and 2 hours, for example, between 2 minutes and 15 minutes. After deposition, the film is heated to a temperature of 600° C. to 800° C. for a time period between 5 minutes and 3 hours.

The substrate preferably includes Si, n-doped Si, p-doped Si, $SiO_2$, $Si_3N_4$, GaAs, MgO, $Al_2O_3$, $ZrO_2$, $SrTiO_3$, $BaTiO_3$, or $PbTiO_3$. The film of Bi-containing metal oxide is deposited on a bottom electrode disposed on the substrate which includes a transistor. The bottom electrode is connected to the transistor by a plug. The bottom electrode may include a metal such as Pt, Pd, Au, Ir, or Rh; a conducting metal oxide such as $IrO_x$, $RhO_x$, $RuO_x$, $OsO_x$, $ReO_x$, or $WO_x$, where $0 \leq x \leq 2$; a conducting metal nitride such as $TiN_x$, $ZrN_x$, or $WN_yTaN_y$, where $0 \leq x \leq 1.0$ and $0 \leq y \leq 1.7$; or a superconducting oxide such as $YBa_2Cu_3O_{7-x}$ where $0 \leq x \leq 1$, and $Bi_2Sr_2Ca_2Cu_3O_{10}$. The bottom electrode may be a Pt electrode.

A first intermediate layer may be provided between the bottom electrode and the plug. Examples of the first intermediate layer include a Ti adhesion layer and a Ti nitride diffusion barrier layer. A second intermediate layer may also be provided between the bottom electrode and the metal oxide layer. Examples of the second intermediate layer include a seed layer, a conducting layer, and a dielectric layer of high permittivity. The plug may include W or Si, and is connected to the bottom electrode and to a source/drain of a MOS field effect transistor. The film may also be used as a thin ferroelectric film for a ferroelectric capacitor, a ferroelectric memory, and/or a ferroelectric field effect transistor, for example, a metal ferroelectric semiconductor or a metal is ferroelectric insulating semiconductor.

The substrate may be flushed with a mixture of an inert gas and the oxidizer before and/or after being exposed to the vapors of the precursors of the metal oxides. The processes of heating, decomposing, and depositing may be performed at least twice on the substrate. The substrate may also be removed from the chamber, treated by at least one intermediate process, such as a rapid thermal process, and returned to the chamber.

The operating conditions of the CVD may also be changed. For example, the compositions of the precursors, oxidizers, and inert gas in the mixture may be varied while the substrate is positioned in the chamber. Deposition temperature as well as the chamber pressure may also be varied. The precursor of Bi oxide may be delivered to the CVD chamber during a period between the onset of deposition and 30 minutes thereafter; the concentration of the Bi oxide is then decreased. In other methods, the substrate may be heated inside the chamber at a temperature lower than 450° C. at least twice, or the substrate may be heated inside the chamber at a temperature lower than 450° C. in the presence of at least one of the oxidizers $O_2$ and $O_3$.

In another aspect, the invention features a method of forming a metal oxide film on a substrate, by heating the substrate to a temperature lower than 450° C. and introducing vapors of a precursor of Bi oxide to the substrate. Bi complexes which include at least one amide group are used as the precursors of Bi oxide. The precursor of Bi oxide decomposes at the surface of the substrate to form Bi oxide, which is deposited on the surface of the substrate.

As used herein, the term "precursor of Bi oxide" means any Bi complex which may be degraded to form Bi oxide. Examples of precursors of Bi oxide include Bi amides, which have the structure $Bi(NR_2)_3$, $Bi(NRR')_3$, or $Bi(NR_2)_2(L)$ where L is NR", alcoxyamine, alkylene diamine, or β-ketoamidate, where each of R, R', and R" is, independently, an alkyl or aryl group. Bi amides also include derivatives of the above-described precursors.

The use of Bi amides as the precursors of Bi oxide in chemical vapor deposition offers numerous advantages. Bi amides contain Bi—N bonds which are relatively easy to cleave. Accordingly, Bi amides can be decomposed at relatively low temperatures. Decomposition and deposition at a lower temperature decreases the migration of Bi oxide to the bottom electrode and the substrate. The degradation of the pre-existing structure is thereby minimized.

Unless otherwise defined, all technical and scientific terms used herein have the same meaning as commonly understood by one of ordinary skill in the art to which this invention belongs. Although methods and materials similar or equivalent to these described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Chemical vapor deposition can be used to provide a thin film of Bi, Sr, and Ta oxides on a surface of a substrate. The substrate can then be used to manufacture devices such as storage cells.

Figure 1:
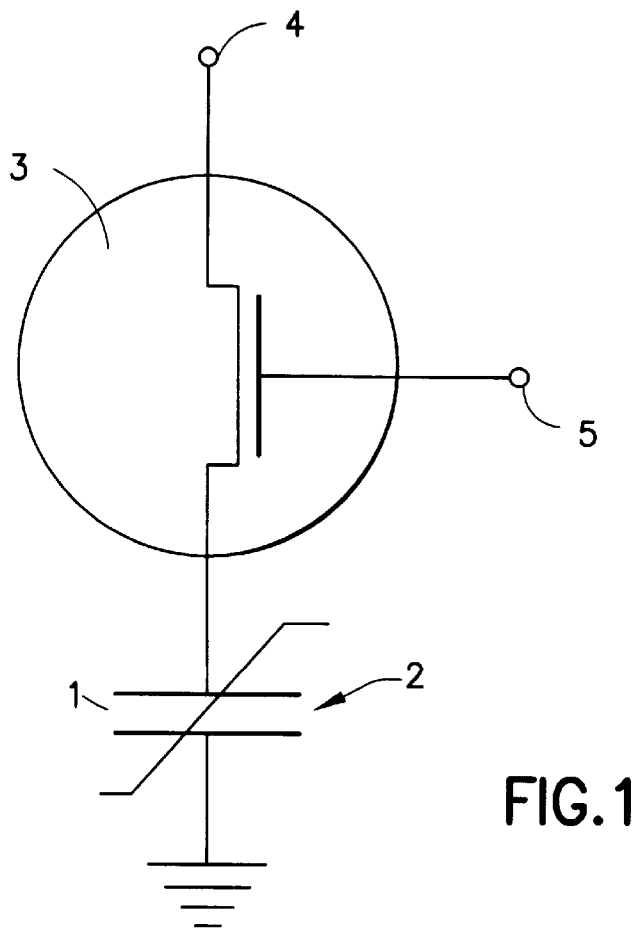
FIG. 1 is a schematic diagram of a storage cell with a ferroelectric memory.

Referring to FIG. 1, a storage cell is formed by placing a layer 1 of ferroelectric material between two plates of a capacitor 2. Capacitor 2 is connected to transistor 3 which has a bit-line 4 and a word-line 5, and which controls access of read-out electronics to capacitor 2. Ferroelectric layer 1 stores information by polarization in a non-volatile manner.

Figure 2:
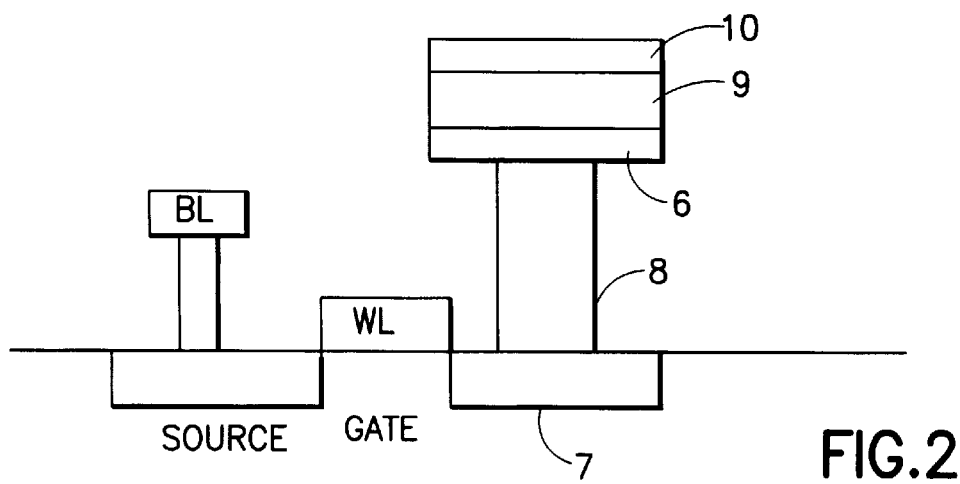
FIG. 2 is a schematic diagram of a SBT layer incorporated into a stack capacitor with a transistor.

Referring to FIG. 2, a ferroelectric SBT layer 9 is incorporated into a stack capacitor with a transistor to form a storage cell. The stack capacitor sits on top of the transistor, and the bottom electrode 6 of the capacitor is connected with a drain of the MOSFET (metal-oxide-semiconductor-field-effect-transistor) by a plug 8 which is made from either poly Si or W. Ferroelectric layer 9 is disposed between the bottom electrode 6 and the top electrode 10.

Chemical vapor deposition (CVD) is used to provide the ferroelectric layers in FIGS. 1 and 2. For example, CVD is used to deposit layers of metal oxides of Bi, Sr, and Ta on a $Pt/Ti/SiO_2/Si$ substrate. During CVD, a substrate is placed in a CVD chamber at a low pressure, and is heated to a deposition temperature. Precursors are vaporized and then delivered to the CVD chamber. Vapors of the precursors are decomposed at the surface of the substrate, and metal oxide molecules are deposited on the substrate to form a thin film. Metal oxide films formed by the CVD process have higher conformality and better step coverage than films produced by other methods. Further advantages of the CVD process include high film uniformity, high film density, the capability to grow very thin films, a high throughput, and low manufacturing costs.

Precursors For Bi Oxides

Bi amides contain Bi—N bonds which are weak enough to undergo decomposition to form Bi oxides at relatively low temperatures. It is believed that the cleavage of these weak Bi—N bonds results in the favorable decomposition mechanism of Bi amides, and subsequent low-temperature deposition of Bi oxides. For example, Bi oxides can be deposited at low temperatures, for example, below 400° C.

The use of Bi amides as precursors of Bi oxides presents an opportunity to produce Bi oxides at relatively low temperatures. The formation of Bi oxide from Bi amides requires $O_2$ during decomposition at the heated substrate. Therefore, the gas phase formation of particles may be controlled by varying the pressure of the oxidizer and by varying the mixing pattern of the vapors and the inert gas in the CVD chamber.

The SBT film obtained using Bi amide as a precursor of Bi oxide exhibits high uniformity of composition within the wafer, high conformity to the structure of the surface, and high run-to-run repeatability. The film of Bi, Sr, and Ta oxides formed by the low temperature deposition is generally non-ferroelectric but can be transformed, by a post-deposition treatment such as annealing, into a ferroelectric Aurivilius phase.

Bi amides used as precursors of Bi oxides generally have the structure $Bi(NR_2)_3$, $Bi(NR_2)_2(L)$, or $Bi(NRR')_3$, where each of R and R' is, independently, $^t$pentyl, pentyl, $^t$Bu, Bu, $^i$Pr, Pr, Et, Me, Ph, aryl, or $SiR''_3$, and where R'' is $^t$Bu, Bu, $^i$Pr, Pr, Et, or Me. Examples of Bi amides include $Bi(NMe_2)_3$, $Bi(NMeEt)_3$, and $Bi(NEt_2)_3$.

Bi amides also include derivatives of the precursors discussed above. They also include derivatives in which the R groups are substituted with donor atoms, such as N, O, or S. For example, a $-CH_2CH_2-N(CH_3)_2$ group may be incorporated into a Bi amide to provide the precursor, $Bi(N-CH_2CH_2-N(CH_3)_2)_3$.

All of these molecules are capable of undergoing oxidative decomposition at very low temperatures. Accordingly, these molecules yield Bi oxides in a controlled and reproducible manner. Additional information regarding the preparation of these precursors may be found in one or more of the following references. A. P. Pisarevskii et al., Inorg. Chem. 35(6), p.84 (1990); W. A. Hermann et al., Chem. Ber. 126, p.1127 (1993); R. G. Goel et al., J. Organomet. Chem. 36, p.323 (1972).

Bi-Containing Metal Oxides

Bi-containing metal oxides deposited on the substrate generally have the following structure:

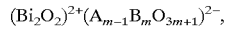

$(Bi_2O_2)^{2+}(A_{m-1}B_mO_{3m+1})^{2-}$, where A is $Bi^{3+}$, $L^{3+}$, $L^{2+}$, $Ca^{2+}$, $Sr^{2+}$, $Ba^{2+}$, $Pb^{2+}$, or $Na^+$, B is $Fe^{3+}$, $Al^{3+}$, $Sc^{3+}$, $Y^{3+}$, $L^{3+}$, $L^{4+}$, $Ti^{4+}$, $Nb^{5+}$, $Ta^{5+}$, $W^{6+}$, or $Mo^{6+}$, where L represents a metal from the lanthanide series, such as $Ce^{4+}$, $La^{3+}$, $Pr^{3+}$, $Ho^{3+}$, $Eu^{2+}$, or $Yb^{2+}$, and m is 1, 2, 3, 4, or 5. These Bi-containing metal oxides are predominantly non-ferroelectric, but can be transformed by an annealing process into ferroelectric oxides with a layered perovskite structure such as the one in the Aurivilius phase. Examples of Bi-containing metal oxides further include:

$Bi_2WO_6$;

$BiMO_3$, where M is Fe or Mn;

$Ba_2BiMO_6$, where M is V, Nb or Ta;

$Pb_2BiMO_6$, where M is V, Nb or Ta;

$Ba_3Bi_2MO_9$, where M is Mo or W;

$Pb_3Bi_2MO_9$, where M is Mo or W;

$Ba_6BiMO_{18}$, where M is Mo or W;

$Pb_6BiMO_{18}$, where M is Mo or W;

$KBiTi_2O_6$; and $K_2BiNb_5O_{15}$.

Additional information regarding the preparation of these metal oxides may be found in one or both of the following references. T. Kodas and M. J. Hampden-Smith, The Chemistry of Metal CVD, Wiley (1994), and W. S. Rees, CVD of Nonmetals, Wiley (1996).

Precursors For Sr Oxides $Sr(thd)_2$ or $Sr(thd)_2$(tetraglyme) is generally used as the precursor of Sr oxide, where thd represents 2,2,6,6,-tetramethyl-heptane-2,5-dionate. Additional ligands of the adduct may be:

polyethers, for example, $R—O—(CH_2CH_2O)_n—R'$, where $2 \leq n \leq 6$, and where each of R and R' is, independently, an alkyl group, an aryl group, or hydrogen; or polyamines, for example, $RNR''—(CH_2CH_2NR'')_n—R'$, where $2 \leq n \leq 6$, where each of R and R' is, independently, alkyl, aryl, or hydrogen, and where R" is H, Me, Et or Pr.

$Sr(thd)_2$ adducts may include adducts with tetraglyme ($MeO—(CH_2CH_2O)_4—Me$), triglyme ($MeO—(CH_2CH_2O)_3—Me$), N,N,N',N",N"-pentamethyl-diethylene-triamine ($Me_2N—(CH_2CH_2NMe)_2—Me$), or N,N,N',N",N"',N"'-hexamethyl-triethylene-tetramine ($Me_2N—(CH_2CH_2NMe)_3—Me$).

Precursors For Ta Oxides

The precursor of Ta oxide generally has the structure $Ta(OR)_{5-n}(X)_n$, where R is Me, Et, Pr, $^i$Pr, Bu, $^i$Bu, $^t$Bu, pentyl, or $^i$pentyl, where X is β-diketonate, and where $1 \leq n \leq 5$. For example, $Ta(O^iPr)_4(thd)$ may be used as the precursor of Ta oxide.

SBT

Strontium bismuth tantalates generally have the structure $SrBi_2Ta_2O_9$, or one of its derivatives, such as:

$SrBi_2Ta_{2-x}Nb_xO_9$, where $0 \leq x \leq 2$;

$SrBi_2Nb_2O_9$;

$Sr_{1-x}Ba_xBi_2Ta_{2-y}Nb_yO_9$, where $0 \leq x \leq 1$ and $0 \leq y \leq 2$;

$Sr_{1-x}Ca_xBi_2Ta_{2-y}Nb_yO_9$ where $0 \leq x \leq 1$ and $0 \leq y \leq 2$;

$Sr_{1-x}Pb_xBi_2Ta_{2-y}Nb_yO_9$, where $0 \leq x \leq 1$ and $0 \leq y \leq 2$;

$Sr_{1-x-y-z}Ba_xCa_yPb_zBi_2Ta_{2-p}Nb_pO_9$, where $0 \leq x \leq 1$, $0 \leq y \leq 1$, $0 \leq z \leq 1$, and $0 \leq p \leq 2$.

SBT's also include the above described compounds in which one or more elements are substituted and/or doped by a metal from the lanthanide series, such as Ce, La, Pr, Ho, Eu, and Yb.

Solution Mixtures

Preferably, liquid delivery CVD is used in the methods of the invention. During liquid delivery CVD, precursors of Bi, Sr, and Ta oxides are dissolved in a solvent or a mixed solution and are then delivered to a vaporizer in a liquid phase. Examples of solvents include, but are not limited to, aliphatic, cycloaliphatic or aromatic solvents, which may have functional groups such as alcohols, ethers, esters, amines, ketones, and/or aldehydes. Mixture of these solvents may also be used, for example, a mixture of THF, $^i$PrOH, and tetraglyme in a ratio of 8:2:1, respectively, and a mixture of octane, decane, and pentamethyl-diethylene-triamine in a ratio of about 5:4:1.

Under some conditions, Bi amides can show a rapid ligand exchange with $Sr(thd)_2$ and $Ta(O^iPr)_4(thd)$. The ligand exchange is not degenerative, but may result in the formation of a poorly characterized mixture of mixed ligand alcoxides and β-diketonate coordinated metal complexes. This exchange can occur at both room temperature and elevated temperatures. The formation of poorly defined mixtures may lead to poor flash vaporization and uncontrolled gas-phase concentrations of the reactants. In addition, storage of the precursor solutions becomes more difficult. If ligand exchange of the precursors is observed, precursors having the same ligand can be used. Alternatively, precursors can be stored in separate solutions which are evaporated in separate vaporizers. Further details are described in a currently pending patent application U.S. Ser. No. 09/107,861, filed Jun. 30, 1998, entitled "Amorphously deposited metal oxide ceramic films," which is hereby incorporated by reference.

Vaporization Process

Precursors of Bi, Sr, and Ta oxides are vaporized prior to the delivery of these oxides to a CVD chamber. Preferably, the precursor of Bi oxide is evaporated separately from the precursors of Sr and Ta oxides. Accordingly, vaporization of the precursors requires at least two flash vaporizers.

Several delivery approaches may be taken in the multiple vaporizer approach. The precursors are stored in separate solutions, each of which is evaporated in a separate vaporizer. The vapors are then mixed and delivered to the substrate surface in the CVD chamber. Alternatively, precursors of Sr and Ta oxides are stored in separate solutions which are mixed prior to vaporization, for example, by a liquid delivery system. The mixed solution is delivered to a single vaporizer. The precursor of Bi oxide is delivered to a second vaporizer. After evaporating the precursors, the vapors are mixed and delivered to the CVD chamber.

In yet another process, precursors of Sr and Ta oxides are stored as a precursor mixture in one solution and delivered to a single vaporizer. Bi amide is delivered to a second vaporizer. After evaporation of the precursors, the vapors are mixed and delivered to the CVD chamber. Alternatively, Bi amide may be vaporized in one vaporizer and precursors of Sr and Ta oxides in a second vaporizer. However, instead of having precursors of Sr and Ta oxides in two separate reservoirs, two solution mixtures are prepared where each contains precursors of Sr and Ta oxides in different concentrations. This allows more accurate mixing of the precursors of Sr and Ta oxides. Additional information regarding the CVD process may be found in one or more of the following references. U.S. patent application Ser. No. 08/758,599, filed Nov. 27, 1996, entitled "Muatiple Vaporizer Reagent Supply System for Chemical Vapor Deposition Utilizing Dissimilar Precursor Composition"; U.S. Pat. No. 5,536,323; U.S. Pat. No. 5,337,651; U.S. Pat. No. 5,431,957; U.S. Pat. No. 5,362,328; and U.S. Pat. No. 5,204,314.

Oxidizer

Precursors of Bi, Sr, and Ta oxides are decomposed in the presence of an oxidizer by oxidative decomposition. $O_2$ is generally used as an oxidizer. However, deposition efficiency may be improved by using more reactive oxidizers during the film deposition. Examples of these alternate oxidizers include singlet $O_2$, $O_3$, $H_2O_2$, $N_2O$, $NO_x$ ($1 \leq x \leq 3$), and downstream oxygen plasma.

The concentration of the oxidizer may be maintained at a level between 5% and 95% of the total gas and vapor flow into the CVD chamber. At least one of $O_2$ and $N_2O$ may be used as the oxidizer. The oxidizer may be supplied to the CVD chamber from an external source such as a tank, bottle, reservoir, or generator, or may be formed in the CVD chamber by converting a molecule therein into an active oxidizer by applying to the CVD chamber plasma, UV light, heat, a sensitizer, or ion beams.

$O_3$ can form oxygen radicals O which can react with the precursors of Bi oxide, Sr oxide, and/or Ta oxide. The reaction may occur in the boundary layer, for example, by inserting the O radical into the Bi—N bonds or by undergoing an electrocyclical bimolecular reaction. When $O_3$ reacts with a precursor containing a phenyl ring, $O_3$ may attack the ring and crack the molecule from another side, yielding an intermediate product such as $O=BiPh_3$, which may either decompose back to $BiPh_3$ or undergo a rearrangement to form a $(PhO)BiPh_2$. Chemical properties of the substrate surface may also be affected by $O_3$. For example, the amount of adsorbed O atoms may be increased, or the electrochemical potential of the surface and its electrical conductivity may be altered. $O_3$ may also affect the chemical properties of the surface of the Bi-containing metal oxide film during its growth in the CVD chamber.

NO and $NO_2$ can react with the precursors already in the boundary layer. In addition, NO and $NO_2$ can be adsorbed on the substrate, react with intermediate products from the decomposition reaction of the precursors, or increase the substrate surface potential for further chemical reactions.

$H_2O_2$ can react with the precursors in the boundary layer or at the heterogenous surface. $H_2O_2$ may form OH and OOH groups on the substrate and provide new decomposition pathways for the precursors.

Singlet $O_2$ ($^1O_2$) is a very effective oxidizer which can be formed by light irradiation of triplet $^3O_2$ in the presence of a sensitizer such as rose bengal or via direct irradiation of $^3O_2$ below 200 nm by, for example, a low pressure Hg lamp/excimer laser.

To form downstream oxygen plasma, the precursor vapor is mixed with an oxygen plasma. The reactive species in the plasma are single O atoms, activated $O_2$ molecules, and $O_3$. The plasma is generated before the oxidizer is mixed with the precursor vapor. This technique effectively modifies CVD processes without direct exposure of the precursors to the high translational energies present in the plasma. G. Lucovsky et al., J. Vac. Sci. Tech. A 4, 681, [1986]; Van Buskirk et al., J. Vac. Sci. Tech. A 10(4), 1578, [1992].

The use of oxidizers offers a number of benefits in depositing the Bi-containing metal oxide film. In general, oxidizers allow low temperature deposition of Bi oxides on the substrate. Oxidizers also stabilize and enhance the deposition of Bi oxides at low pressures. Oxidizers also help in depositing the Bi-containing metal oxide film in a desirable phase.

CVD Process

The substrate is heated to a deposition temperature ranging from 300° C. to 500° C. Preferably, the substrate is heated to a temperature below 450° C. The pressure in the chamber is maintained between 0.1 and 10 torr. A carrier gas such as Ar, He, or $N_2$, and oxidizers such as $O_2$, singlet $O_2$, $O_3$, $N_2O$, $NO_x(1 \leq x \leq 3)$, and downstream oxygen plasma are also delivered to the CVD chamber. The total gas flow is maintained between 1 and 15,000 sccm, where sccm represents a volumetric flow rate in the unit of cc/min measured at the standard condition, that is, at 0° C. and 1 atm. The deposition time ranges from 30 to 60 minutes.

CVD processes for SBT can be carried out at different deposition temperatures. For example, the CVD process at a temperature such as 430° C. yields a non-ferroelectric film in the fluorite phase. By annealing between 600° C. and 820° C., for example, at 750° C. for one hour, this film is converted into the ferroelectric Aurivilius phase. The structure of the deposited film depends on many different deposition parameters, although the deposition temperature has the most profound effect. For example, films deposited at lower temperatures, for example, at 350° C., are predominately amorphous.

At high temperatures, for example, 650° C., the CVD process yields films which are in a crystalline non-ferroelectric phase, such as a fluorite phase, or which are already in the ferroelectric Aurivilius phase. By annealing at 800° C. (ferroanneal), the non-ferroelectric SBT layer can be transformed into the ferroelectric Aurivilius phase, or the electrical properties of the existing ferroelectric films can be enhanced.

Alternatively, the deposition may be carried out under two different conditions. For example, it may be advantageous to deposit more Bi oxides in the beginning of the CVD process than during the rest of the process to compensate for a loss of Bi oxides due to depletion into the bottom electrode during deposition and/or annealing. It may also be helpful to have a nucleation control in the beginning, even if this decreases the growth rate. After the nucleation step, the conditions are changed for a high growth rate in the second deposition step. Nucleation is very important for phase control and can be very important for composition control, for example, if the film composition depends on the nature of the surface.

EXAMPLE 1

TGA and DSC Study Results

STA, a combination of thermogravimetric analysis (TGA) and differential scanning calorimetry (DSC), was performed in both argon and oxygen atmospheres.

Bi amides were monomeric in the vapor phase according to mass spectrometry and were readily vaporized upon mild heating under vacuum. A series of Bi amides were synthesized and purified by distillation, sublimation or crystallization.

Figure 3:
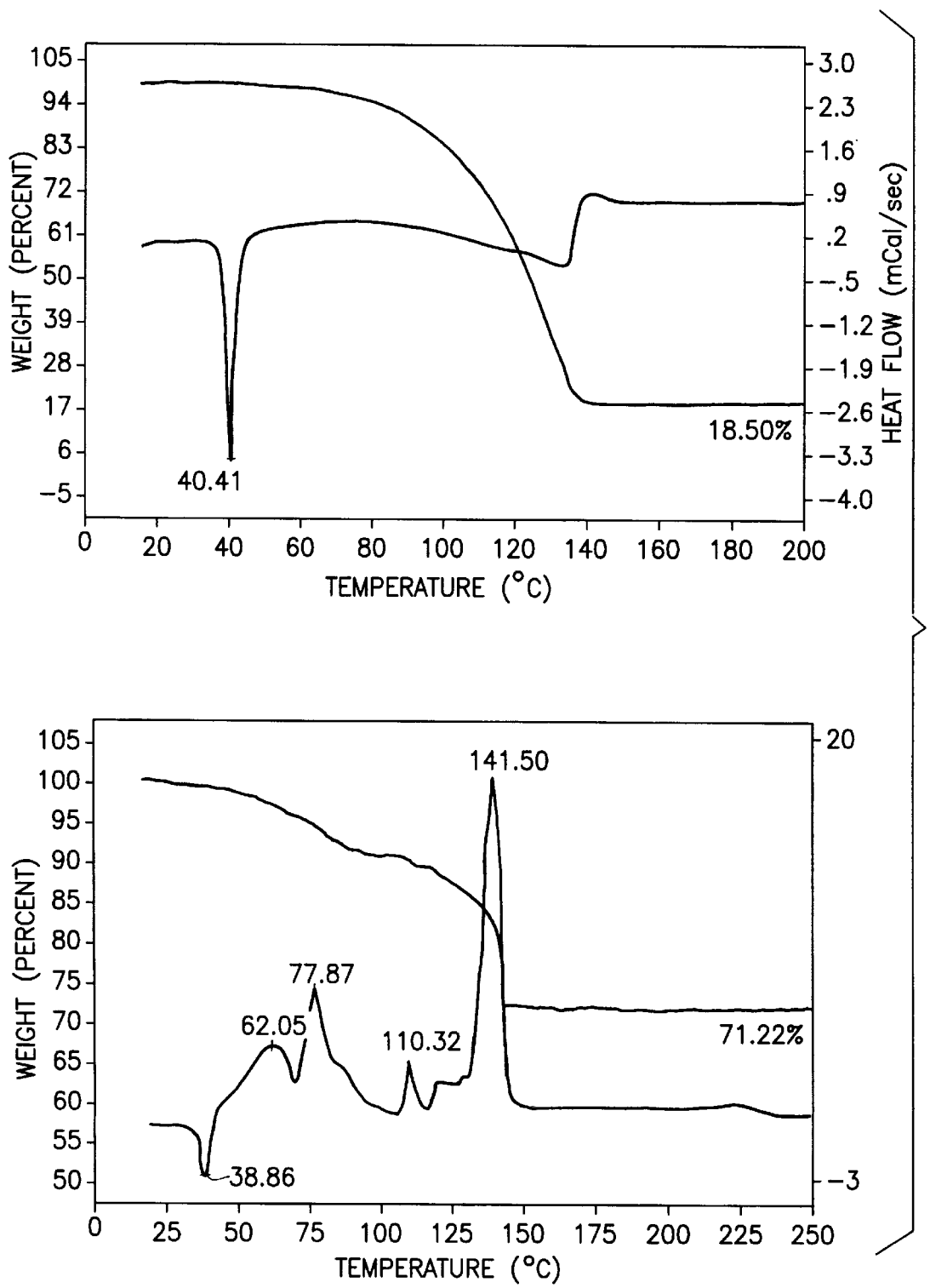
FIG. 3 is a graph showing the STA results of $Bi(NMe_2)_3$ in Ar (left) and $O_2$ (right).
Figure 4:
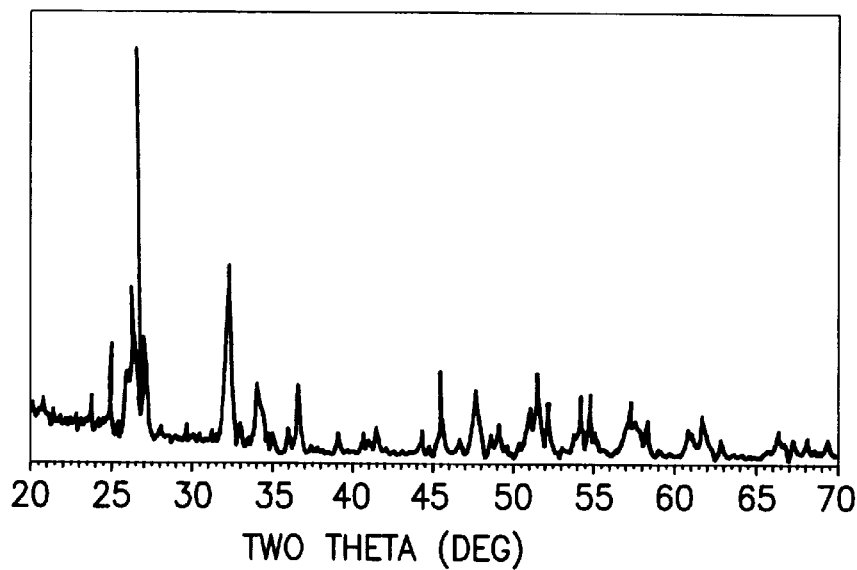
FIG. 4 is a graph showing the XRD results of $\alpha\text{-}Bi_2O_3$ from oxidation of $Bi(NMe_2)_3$ after heating to 500° C.

$Bi(NMe_2)_3$ was prepared as reported in the literature. Clegg, W. et al.; X-ray Crystal Structure of $[Bi(NMe_2)_3]$, Inorganic Chemistry 1991; 30(24), pp. 4680–4682. The $^1H$ NMR spectrum consisted of a singlet at 3.45 ppm in $C_6D_6$, indicating that all of the methyl groups were equivalent at room temperature. $Bi(NMe_2)_3$ was stable indefinitely when stored at −40° C., under an inert atmosphere, in the dark. However, the material was photolytically, oxidatively, and hydrolytically unstable. The surface of $Bi(NMe_2)_3$ became black upon storage under fluorescent lights, and it smoked upon exposure to air. $Bi(NMe_2)_3$ hydrolyzed readily to form an insoluble white precipitate and free dimethylamine, $NHMe_2$. FIG. 3 shows the STA results of $Bi(NMe_2)_3$ in Ar (left) and $O_2$ (right). In Ar, $Bi(NMe_2)_3$ melted at 40° C. followed by sublimation between 60° C. and 140° C. at atmospheric pressure. In $O_2$, decomposition of $Bi(NMe_2)_3$ began immediately after melting. Multiple exotherms were observed up to 140° C., where the transformation to $Bi_2O_3$ was essentially complete, based upon weight loss. A small (1%) drop in weight was observed at 425° C. (not shown), perhaps due to the annealing of excess carbon from the residue or loss of Bi due to evaporation. As shown in FIG. 4, the powder XRD of material heated to 500° C. in $O_2$ revealed the material to be $\alpha$-$Bi_2O_3$.

$Bi(NEt_2)_3$ was prepared as reported in the literature. Clegg, W. et al.; X-ray Crystal Structure of $[Bi(NMe_2)_3]$, Inorganic Chemistry 1991; 30(24), pp. 4680–4682. The $^1$H NMR spectrum consisted of a quadruplet at 3.74 ppm and a triplet at 1.14 ppm in $C_6D_6$, indicating that all of the ethyl groups were equivalent at room temperature. As with the methyl analog, $Bi(NEt_2)_3$ decomposed photolytically to a black insoluble material. $Bi(NEt_2)_3$ was too air sensitive to allow for the acquisition of the STA data.

Figure 5:
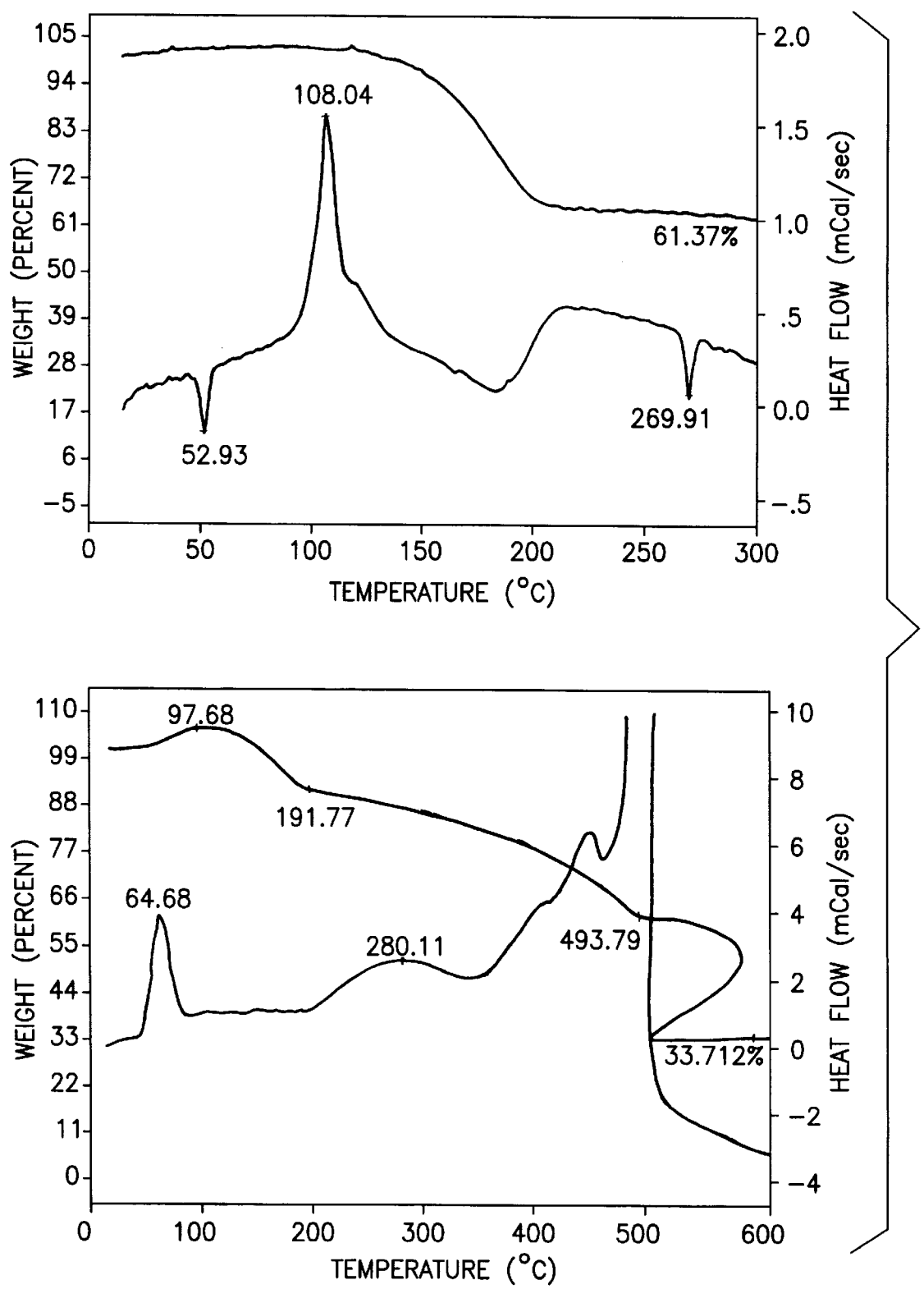
FIG. 5 is a graph showing the STA results of $Bi(NPh_2)_3$ in Ar (left) and $O_2$ (right).

$Bi(NPh_2)_3$ was prepared as reported in the literature and recrystallized. Clegg, W. et al.; X-ray Crystal Structure of $[Bi(NMe_2)_3]$, Inorganic Chemistry 1991; 30(24), pp. 4680–4682. The $^1$H NMR spectrum consisted of a multiplet at 7.04 ppm and another at 6.72 ppm in $C_6D_6$, indicating that all of the phenyl groups were equivalent at room temperature. $Bi(NPh_2)_3$ was not photolytically sensitive, but did not hydrolyze readily to form an insoluble precipitate and to free diphenylamine, $NHPh_2$. The X-ray crystal structure of $Bi(NPh_2)_3$ was similar to that of $Bi(NMe_2)_3$. Attempts at sublimation under vacuum were unsuccessful, resulting in decomposition to a black liquid with the evolution of a colorless, volatile material. FIG. 5 shows the STA results of $Bi(NPh_2)_3$ in Ar (left) and $O_2$ (right). In Ar, the STA revealed an endotherm at 53° C. followed by a decomposition exotherm at 108° C., and a second endotherm at 270° C. A capillary melting point observation suggested that the first endotherm was due to a solid-solid phase transition, while decomposition/melting occurred between 100° C. and 113° C. The endotherm at 270° C. was not examined further. The volatile decomposition product sublimed between 120° C. and 200° C. leaving a 61 wt % residue at 300° C. The byproducts were not identified, but the mass loss did not appear to correspond to biphenyl ($Ph_2$), azobenzene (PhNNPh), or tetraphenylhydrazine ($Ph_2NNPh_2$). In $O_2$, the STA revealed a reaction beginning at 50° C., with a maximum exotherm at ca. 65° C. that was associated with the addition of ca. 3–5 wt %. This material decomposed between 125° C. and 190° C., losing 14 wt %. A slow decomposition then occurred between 190° C. and 490° C. accompanied by 20–25 wt % loss. At 500° C., the sample exploded, yielding a large exotherm. The remaining material (residue 34 wt %) corresponded well with the expected amount, if $Bi_2O_3$ (calculated 33 wt %) was formed. The composition of the oxidation product was riot identified by the powder XRD.

$Bi(N(SiMe_3)_2)_3$ was prepared as reported in the literature. Clegg, W. et al.; X-ray Crystal Structure of $[Bi(NMe_2)_3]$, Inorganic Chemistry 1991; 30(24), pp. 4680–4682. The product was purified by sublimation at 100° C. and 100 mtorr. The $^1$H NMR spectrum consisted of a single resonance at 0.36 ppm in $C_6D_6$, indicating that all of the trimethylsilyl groups were equivalent at room temperature. $Bi(N(SiMe_3)_2)_3$ hydrolyzed readily to form an insoluble precipitate and to free hexamethyldisilazane ($NH(SiME_3)_2$), observed at 0.09 ppm in $C_6D_6$. The originally reported melting/decomposition temperature of 90° C. was incorrect.

Figure 6:
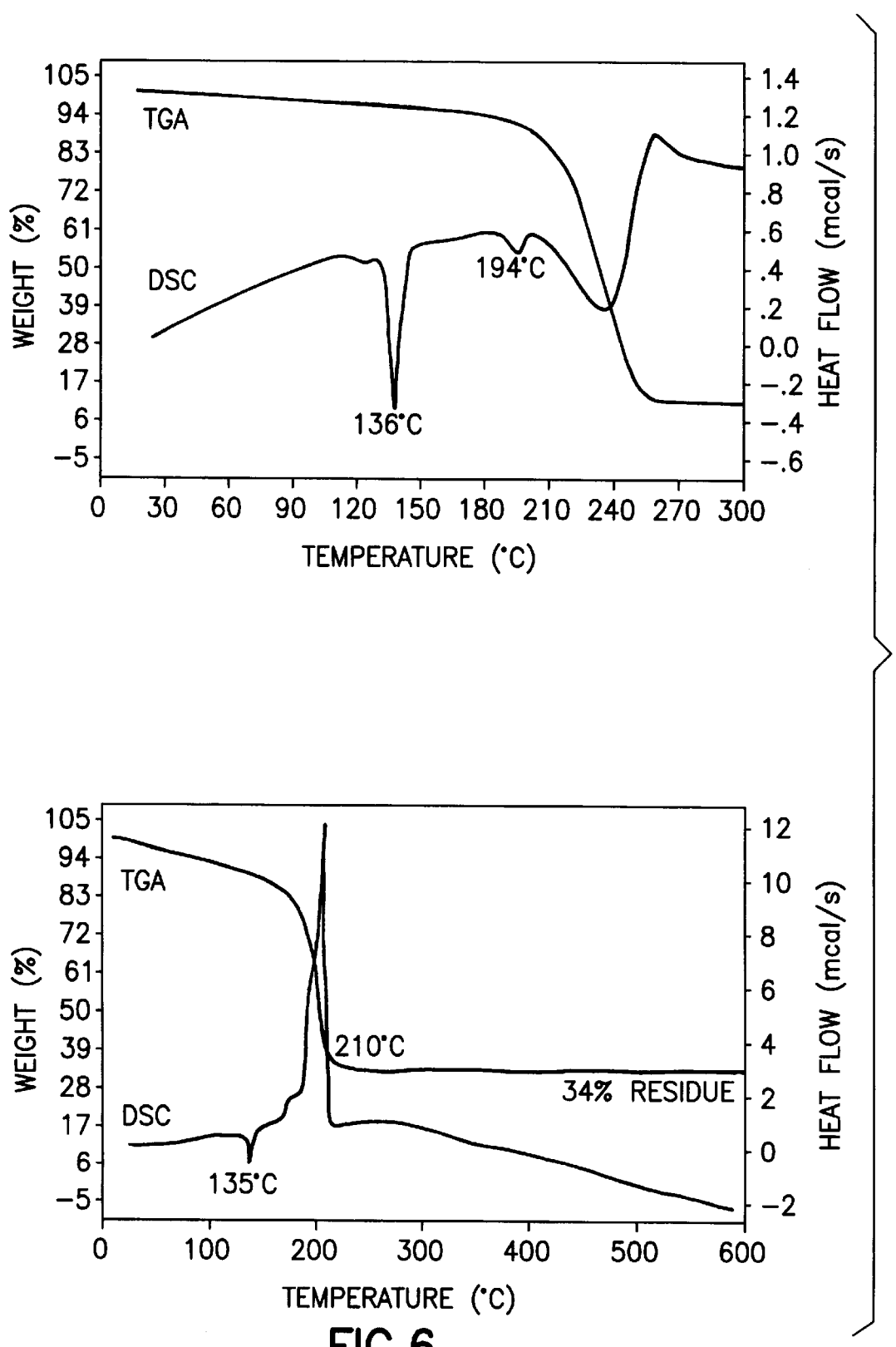
FIG. 6 is a graph showing the STA results of $Bi(N(SiMe_3)_2)_3$ in Ar (left) and $O_2$ (right).
Figure 7:
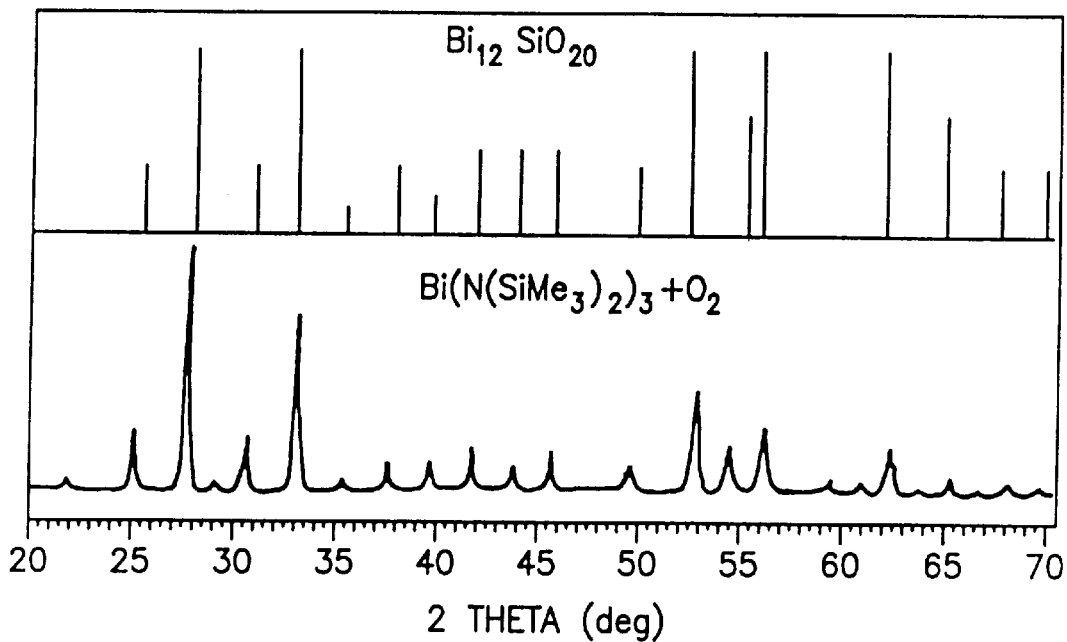
FIG. 7 is a graph comparing the powder XRD of the oxidation product of $Bi(N(SiMe_3)_2)_3$ to $Bi_{12}O_{20}Si$.
Figure 8:
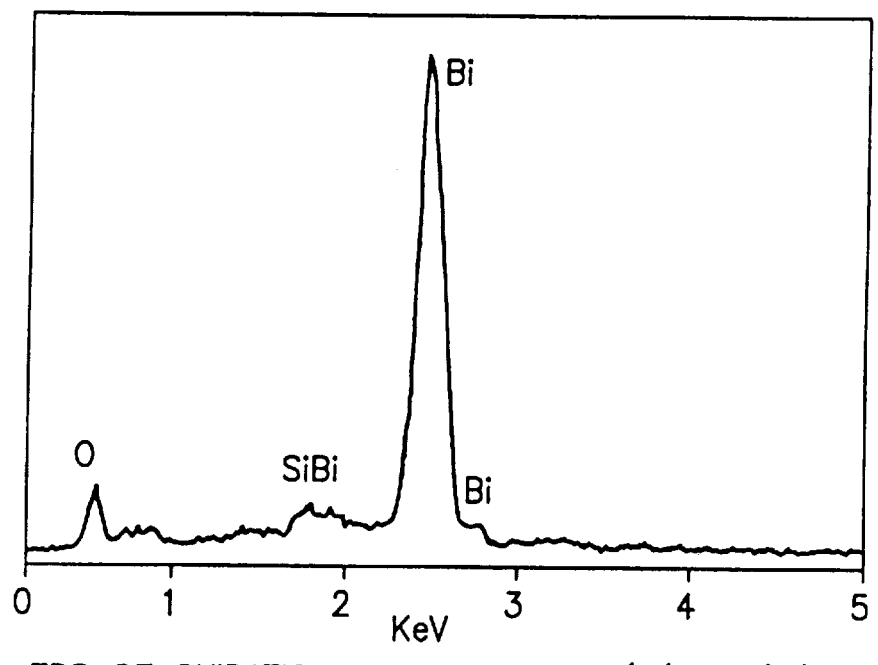
FIG. 8 is a graph showing the EDS results of the oxidation product of $Bi(N(SiMe_3)_2)_3$.

FIG. 6 shows the STA results of $Bi(N(SiMe_3)_2)_3$ in Ar (left) and $O_2$ (right). In Ar, a solid-solid phase transition was observed at 136° C., and $Bi(N(SiMe_3)_2)_3$ melted at 185° C. according to the DSC. The melting point was confirmed by capillary melting point measurement. Sublimation occurred between 220° C. and 270° C. at atmospheric pressure. In $O_2$, decomposition occurred between 150° C. and 220° C. The product of the thermal oxidation was examined by powder XRD as shown in FIG. 7. The product was found to be a Bi oxide distinct from $\alpha$-$Bi_2O_3$.

EXAMPLE 2

Low-Temperature CVD Process

A $Pt/Ti/SiO_2/Si$ substrate (100 nm Pt on 10 nm Ti) is placed in a CVD chamber. The temperature of the substrate is maintained by a resistivity heater and kept between 300° C. and 500° C., for example, 430° C. The chamber pressure is between 0.5 and 5 torr, for example, 1 torr. The total gas flow is between 500 and 2,000 sccm, for example, 1,300 sccm. $O_2$ is used as an oxidizer. The amount of $O_2$ is between 20% and 80% of the total gas flow, for example 40%. The deposition time is 30 to 60 min.

$Bi(NMe_2)_3$ (bismuth tris(dimethylamide)), $Sr(thd)_2$ (tetraglyme), and $Ta(O^iPr)_4(thd)$ are used as precursors of Bi oxide, Sr oxide, and Ta oxide, respectively. Precursors of Sr oxide and Ta oxide are stored in a solution of THF, $^iPrOH$, and tetraglyme in a ratio of 8:2:1, respectively. The concentrations in the solution are 0.3 molar Ta precursor and 0.15 molar Sr precursor. This solution is delivered by a pump to a flash-vaporizer and evaporated on a stainless-steel frit at a temperature between 210° C. and 230° C. A precursor solution delivery rate is 0.05–0.30 ml/min, for example, 0.15 ml/min. A carrier gas such as Ar is also delivered at a rate of 200–800 sccm, for example, 400 sccm. For a frit 1.6 cm in diameter, these flow rates give efficient evaporation results.

In a second approach, $Bi(NMe_2)_3$ is stored separately in a solution of octane. The concentration of Bi amide is, for example, 0.1 molar. This solution is delivered to a second vaporizer which is maintained at a temperature of 200° C. For a stainless steel frit 1.6 cm in diameter, a liquid delivery rate of 0.05–0.30 ml/min, for example, 0.15 ml/min is used, and a carrier gas flow of 200–800 sccm, for example, 400 sccm is used. After vaporization, vapors of the precursors of Sr oxide and Ta oxide are mixed with Bi amide vapors. These vapors are delivered to a CVD chamber through a showerhead in which they are mixed with $O_2$ and with additional Ar in order to adjust total gas flow and $O_2$ content. Gas flow rates are 4000 sccm of Ar carrier for the precursors of Sr oxide and Ta oxide, 300 sccm of Ar carrier for Bi amide, 180 sccm of additional Ar, and 520 sccm of $O_2$.

After the CVD process, the film is annealed at 750° C. for 60 minutes or at 800° C. for 15 minutes to form the ferroelectric Aurivilius phase.

EXAMPLE 3

High-Temperature CVD Process

Chemical vapor deposition is also carried out at higher temperatures, for example, at 600° C. Precursors and deposition conditions are the same as those used in the low temperature process. The high-temperature process results in a film which was in a non-ferroelectric fluorite phase, in a ferroelectric Aurivilius phase, or in a mixture of these phases.

After the CVD process, the deposited film is annealed at 750° C. for 60 minutes or at 800° C. for 15 minutes in order to form and/or to completely crystallize the ferroelectric Aurivilius phase.

EXAMPLE 4

Multi-Step CVD Process

A multi-step process is also used, where a different deposition condition is applied for the first 2–10 minutes in order to yield a higher Bi content in the parts of the film adjacent to the Pt bottom electrode than in the rest of the film. An increased amount of the precursor of Bi oxide is delivered to the CVD chamber for the first 2–10 minutes, for example, by increasing the liquid delivery rate of the second, Bi amide vaporizer. All other parameters in this step, and all parameters for the second step, are the same as those used in the single-step process.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of forming a film comprising Bi oxide on a substrate, said method comprising:
   decomposing a precursor of Bi oxide to form Bi oxide, wherein said precursor of Bi oxide comprises at least one amide group; and
   depositing said Bi oxide on said substrate;
   wherein said precursor of Bi oxide is dissolved in a solution prior to being decomposed.

2. The method of claim 1, wherein said steps of decomposing said precursor and depositing said Bi oxide take place at a temperature lower than 450° C.

3. The method of claim 1, wherein said substrate comprises at least one of Si, n-doped Si, p-doped Si, $SiO_2$, $Si_3N_4$, GaAs, MgO, $Al_2O_3$, $ZrO_2$, $SrTiO_3$, $BaTiO_3$, and $PbTiO_3$.

4. The method of claim 1, further comprising:
   decomposing a precursor of Sr oxide and a precursor of Ta oxide at a temperature lower than 450° C. to form Sr oxide and Ta oxide, respectively; and
   simultaneously depositing said Bi oxide, said Sr oxide and said Ta oxide on said substrate at a temperature lower than 450° C.

5. The method of claim 4, wherein said method further comprises:
   placing said substrate in a chamber;
   heating said substrate to a deposition temperature lower than 450° C.;
   introducing vapors of said precursor of Bi oxide, said precursor of Sr oxide, and said precursor of Ta oxide into said chamber;
   decomposing said precursors of Bi oxide, Sr oxide, and Ta oxide into said oxides thereof; and
   depositing said oxides on said substrate.

6. The method of claim 5, wherein the decomposition of said precursors comprises:
   introducing an oxidizer into said chamber; and
   converting said precursors into said oxides by oxidative decomposition.

7. The method of claim 6, wherein said oxidizer comprises at least one of $O_2$, singlet $O_2$, $O_3$, $H_2O_2$, $N_2O$, $NO_x$, where x is 1, 2, or 3, and downstream oxygen plasma.

8. The method of claim 7, wherein said oxidizer occupies between 5% and 95% of the total gas and vapor flow into said chamber.

9. The method of claim 7, wherein said oxidizer comprises at least one of $O_2$ and $N_2O$.

10. The method of claim 6, wherein at least two different oxidizers are introduced into said chamber.

11. The method of claim 6, wherein said oxidizer is formed by converting a molecule in said chamber into an active oxidizer by applying at least one of a plasma, UV light, heat, a sensitizer, and ion beams.

12. The method of claim 6, wherein an additional inert gas is added to said chamber, said inert gas comprising at least one of Ar, He, and $N_2$, and wherein said additional inert gas occupies between 10% and 90% of the total gas and vapor flow into said chamber.

13. The method of claim 6, wherein said substrate is flushed with a mixture of an inert gas and said oxidizer before being exposed to said vapors of said precursors of said metal oxides.

14. The method of claim 6, wherein said substrate is flushed with a mixture of an inert gas and said oxidizer after being exposed to said vapors of said precursors.

15. The method of claim 6, wherein said substrate is removed from said chamber, treated by at least one intermediate process, and returned to said chamber.

16. The method of claim 6, wherein the composition of said oxidizer is varied while said substrate is positioned in said chamber.

17. The method of claim 6, wherein said vapors of said precursors, said oxidizers, and an inert gas comprising at least one of Ar, He, and $N_2$ are introduced to said chamber at a total flow rate of 1 ml/min to 15,000 ml/min, measured at the standard condition.

18. The method of claim 5, wherein said oxides are deposited at a temperature between 300° C. and 450° C.

19. The method of claim 5, wherein the pressure in said chamber is between 0.001 and 760 torr.

20. The method of claim 19, wherein the pressure in said chamber is between 0.1 and 10 torr.

21. The method of claim 5, wherein at least one of said processes of heating, decomposing and depositing is performed at least twice on said substrate.

22. The method of claim 5, wherein said deposition temperature is varied while said substrate is positioned in said chamber.

23. The method of claim 5, wherein the pressure in said chamber is varied while said substrate is positioned in said chamber.

24. The method of claim 5, wherein said substrate is heated inside said chamber at a temperature lower than 450° C. at least twice.

25. The method of claim 5, wherein said substrate is heated inside said chamber at a temperature lower than 450° C. in the presence of at least one of $O_2$ and $O_3$.

26. The method of claim 4, wherein said film comprises a compound selected from the group consisting of:
   $SrBi_2Ta_2O_9$;
   $SrBi_2Ta_{2-x}Nb_xO_9$, wherein $0 \leq y \leq 2$;
   $SrBi_2Nb_2O_9$;
   $Sr_{1-x}Ba_xBi_2Ta_{2-y}Nb_yO_9$, wherein $0 \leq x \leq 1$ and $0 \leq y \leq 2$;
   $Sr_{1-x}Ca_xBi_2Ta_{2-y}Nb_yO_9$ wherein $0 \leq x \leq 1$ and $0 \leq y \leq 2$;
   $Sr_{1-x}Pb_xBi_2Ta_{2-y}Nb_yO_9$, wherein $0 \leq x \leq 1$ and $0 \leq y \leq 2$; and
   $Sr_{1-x-y-z}Ba_xCa_yPb_zBi_2Ta_{2-p}Nb_pO_9$, wherein $0 \leq x \leq 1$, $0 \leq y \leq 1$, $0 \leq z \leq 1$, and $0 \leq p \leq 2$.

27. The method of claim 26, wherein at least one element of said compound is substituted by a metal selected from the group consisting of Ce, La, Pr, Ho, Eu, and Yb.

28. The method of claim 4, wherein said precursor of Sr oxide is $Sr(thd)_2$ or $Sr(thd)_2$ adduct.

29. The method of claim 28, wherein said precursor of Sr oxide comprises at least one of a polyether and a polyamine.

30. The method of claim 29, wherein said polyether has the formula R—O—$(CH_2CH_2O)_n$—R', wherein $2 \leq n \leq 6$, and wherein each of R and R' is, independently, an alkyl group, an aryl group, or hydrogen.

31. The method of claim 29, wherein said polyamine has the formula R—NR"—$(CH_2CH_2NR")_n$—R', wherein $2 \leq n \leq 6$, wherein each of R and R' is, independently, an alkyl group, an aryl group, or hydrogen, and wherein R" is H, Me, Et or Pr.

32. The method of claim 29, wherein said precursor of Sr oxide comprises at least one of tetraglyme, triglyme, N,N, N',N",N"-pentamethyl-diethylene-triamine, and N,N,N',N", N'",N'"-hexamethyl-triethylene-tetramine.

33. The method of claim 4, wherein said precursor of Ta oxide has the formula $Ta(OR)_{5-n}(X)_n$, wherein R is Me, Et, Pr, $^i$Pr, Bu, $^i$Bu, $^t$Bu, pentyl, or $^t$pentyl, wherein X is β-diketonate, and wherein n is 1, 2, 3, 4, or 5.

34. The method of claim 33, wherein said precursor of Ta oxide is $Ta(O^iPr)_4(thd)$.

35. The method of claim 33, wherein the composition of said inert gas in said mixture is varied while said substrate is position in said chamber.

36. The method of claim 4, wherein at least one of said precursors is dissolved in a solution comprising at least one of an aliphatic, cycloaliphatic, and an aromatic solvent,
said solvent having at least one functional group selected from the group consisting of an alcohol, ether, ester, amine, ketone, and aldehyde group.

37. The method of claim 36, wherein said precursors of Sr oxide and Ta oxide are dissolved in a mixture of THF, $^i$PrOH, and tetraglyme in a ratio of about 8:2:1, respectively.

38. The method of claim 36, wherein said precursors of Sr oxide and Ta oxide are dissolved in a mixture of octane, decane, and pentamethyl-diethylene-triamine in a ratio of about 5:4:1, respectively.

39. The method of claim 36, wherein said precursors of Sr oxide and Ta oxide are dissolved in butylacetate.

40. The method of claim 36, wherein said precursor of Bi oxide is dissolved in octane.

41. The method of claim 36, wherein said solution is evaporated by at least one vaporizer.

42. The method of claim 41, wherein said solution is evaporated at a temperature from 130° C. to 300° C.

43. The method of claim 41, wherein said solution is evaporated at a temperature from 170° C. to 240° C.

44. The method of claim 41, wherein an inert gas is added to the vapors of said solution and a mixture of said inert gas and vapors is delivered to said chamber, said inert gas comprising at least one of Ar, He, and $N_2$.

45. The method of claim 44, wherein said mixture comprises vapors of said precursors of Bi oxide, Sr oxide, and Ta oxide in a ratio of about 2:1:2.

46. The method of claim 41, wherein vapors consisting essentially of said precursor of Bi oxide are delivered to said chamber during a period between the onset of deposition and 30 minutes thereafter.

47. The method of claim 36, wherein the composition of said precursors in said mixture is varied while said substrate is positioned in said chamber.

48. The method of claim 4, wherein said oxides are deposited onto said substrate over a time period between 2 minutes and 2 hours.

49. The method of claim 48, wherein said oxides are deposited onto said substrate over a time period between 2 minutes and 15 minutes.

50. The method of claim 1, further comprising converting said film into a ferroelectric film by an annealing process.

51. The method of claim 50, wherein said film is heated to a temperature between 600° C. and 800° C. for a time period between 5 minutes and 3 hours.

52. The method of claim 1, wherein said film is deposited as a ferroelectric film.

53. The method of claim 1, wherein said precursor of Bi oxide has the formula $Bi(NR_2)_3$, $Bi(NR_2)_2(L)$, or $Bi(NRR')_3$, wherein L is NR", alcoxyamine, alkylene diamine, or β-ketoamidate, and wherein each of R, R', and R" is, independently, an alkyl group or an aryl group.

54. The method of claim 53, wherein said precursor of Bi oxide is $Bi(NR_2)_3$, wherein R is $^t$pentyl, pentyl, $^t$Bu, Bu, $^i$Pr, Pr, Et, Me, Ph, aryl, or $SiR"_3$, and wherein R" is $^t$Bu, Bu, $^i$Pr, Pr, Et, or Me.

55. The method of claim 1, wherein said precursor of Bi oxide comprises a donor atom selected from the group consisting of N, O, and S.

56. The method of claim 1, wherein said film comprises at least one of Ca, Ba, Pb, Na, Fe, Al, Sc, Y, Ti, Nb, W, Mo, Ce, La, Pr, Ho, Eu, and Yb.

57. The method of claim 56, wherein said film comprises a compound having the formula

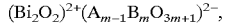

wherein A is $Bi^{3+}$, $L^{3+}$, $L^{2+}$, $Ca^{2+}$, $Sr^{2+}$, $Ba^{2+}$, $Pb^{2+}$, or $Na^+$, B is $Fe^{3+}$, $Al^{3+}$, $Sc^{3+}$, $Y^{3+}$, $L^{3+}$, $L^{4+}$, $Ti^{4+}$, $Nb^{5+}$, $Ta^{5+}$, $W^{6+}$, or $Mo^{6+}$, wherein L is selected from the group consisting of $Ce^{4+}$, $La^{3+}$, $Pr^{3+}$, $Ho^{3+}$, $Eu^{2+}$ and $Yb^{2+}$, and m is 1, 2, 3, 4, or 5.

58. The method of claim 1, wherein said film comprises a compound selected from the group consisting of:
$Bi_2WO_6$;
$BiMO_3$, where M is Fe or Mn;
$Ba_2BiMO_6$, where M is V, Nb or Ta;
$Pb_2BiMO_6$, where M is V, Nb or Ta;
$Ba_3Bi_2MO_9$, where M is Mo or W;
$Pb_3Bi_2MO_9$, where M is Mo or W;
$Ba_6BiMO_{18}$, where M is Mo or W;
$Pb_6BiMO_{18}$, where M is Mo or W;
$KBiTi_2O_6$; and
$K_2BiN_5O_{15}$.

59. The method of claim 1, wherein said film is deposited on a bottom electrode disposed on said substrate,
said substrate comprising a transistor therein,
said bottom electrode being connected to said transistor by a plug.

60. The method of claim 59, wherein said film is used as a thin ferroelectric film for a ferroelectric capacitor.

61. The method of claim 59, wherein said bottom electrode comprises at least one of:
a metal selected from the group consisting of Pt, Pd, Au, Ir, and Rh;
a conducting metal oxide selected from the group consisting of $IrO_x$, $RhO_x$, $RuO_x$, $OsO_x$, $ReO_x$, $WO_x$, wherein x is 0, 1 or 2;
a conducting metal nitride selected from the group consisting of $TiN_x$, $ZrN_x$, and $WN_yTaN_y$, wherein $0 \leq x \leq 1.0$ and $0 \leq y \leq 1.7$; and
a superconducting oxide selected from the group consisting of $YBa_2Cu_3O_{7-x}$ where $0 \leq x \leq 1$, and $Bi_2Sr_2Ca_2Cu_3O_{10}$.

62. The method of claim 59, wherein said bottom electrode is a Pt electrode.

63. The method of claim 59, wherein at least one first intermediate layer is provided between said bottom electrode and said plug, said first intermediate layer comprising at least one of an adhesion layer and a diffusion barrier layer.

64. The method of claim 59, wherein at least one second intermediate layer is provided between said bottom electrode and said metal oxide film, said second intermediate layer comprising at least one of a seed layer, a conducting layer, and a dielectric layer.

65. The method of claim 59, wherein said plug is connected to said bottom electrode and to a drain of a MOS ferroelectric effect transistor, said plug consisting essentially of W or Si.

66. The method of claim 59, wherein said film is used as a thin ferroelectric film for a ferroelectric memory.

67. The method of claim 66, wherein said film is used as a thin ferroelectric film for a ferroelectric field effect transistor.

68. A method of forming a film on a substrate, said method comprising:

heating said substrate to a temperature lower than 450° C.; and introducing vapors of a precursor of Bi oxide to said substrate, wherein said precursor of Bi oxide comprises at least one amide group, said precursor decomposing at the surface of said substrate to form Bi oxide, said Bi oxide being deposited on the surface of said substrate;

wherein said precursor of Bi oxide is dissolved in a solution prior to being decomposed.

\* \* \* \* \*